United States Patent [19]

Edgren et al.

[11] Patent Number: 4,786,503
[45] Date of Patent: Nov. 22, 1988

[54] DOSAGE FORM COMPRISING PARALLEL LAMINE

[75] Inventors: David E. Edgren, El Granada; Judy A. Magruder, Palo Alto; Gurdish K. Bhatti, Fremont, all of Calif.

[73] Assignee: ALZA Corporation, Palo Alto, Calif.

[21] Appl. No.: 34,971

[22] Filed: Apr. 6, 1987

[51] Int. Cl.⁴ .......................... A61K 9/70; A61K 9/24
[52] U.S. Cl. ....................................... 424/443; 424/472
[58] Field of Search ...................... 424/472, 473, 443

[56] References Cited

U.S. PATENT DOCUMENTS

| | | | |
|---|---|---|---|
| 3,870,790 | 3/1975 | Lowey et al. | 424/19 |
| 4,140,755 | 2/1979 | Sheth et al. | 424/21 |
| 4,167,558 | 9/1979 | Sheth et al. | 424/22 |
| 4,226,849 | 10/1980 | Schor | 424/19 |
| 4,259,314 | 3/1981 | Lowey | 424/19 |
| 4,357,469 | 11/1982 | Schor | 536/91 |
| 4,369,172 | 1/1983 | Schor et al. | 424/19 |
| 4,389,393 | 6/1983 | Schor et al. | 424/19 |
| 4,454,108 | 6/1984 | Iida et al. | 424/472 |
| 4,540,566 | 9/1985 | Davis et al. | 424/22 |
| 4,610,870 | 9/1986 | Jain et al. | 424/473 X |

FOREIGN PATENT DOCUMENTS

74584 3/1983 European Pat. Off. ............ 424/472

Primary Examiner—Michael Lusignan
Attorney, Agent, or Firm—Paul L. Sabatine; Edward L. Mandell; Steven F. Stone

[57] ABSTRACT

A bilaminated dosage form is disclosed comprising at least 30 weight percent cellulose ether, a first lamina and a second lamina with each lamina comprising a different cellulose ether formulation, and a drug in at least one of the lamina.

26 Claims, 3 Drawing Sheets

DOSAGE FORM COMPRISING PARALLEL LAMINE

CROSS-REFERENCE TO COPENDING APPLICATION

This patent application is copending with a patent application Ser. No. 07/039,405 filed Apr. 17, 1987.

FIELD OF THE INVENTION

This invention pertains to a sustained release dosage form. More particularly, the invention concerns a dosage form comprising a first lamina and a second lamina in laminated arrangement. The first lamina comprises a cellulose ether composition and the second lamina comprises a different cellulose ether composition with the amount of cellulose ether composition in the dosage form exceeding thirty weight percent. A dosage amount of drug is present in at least one of the lamina.

BACKGROUND OF THE INVENTION

Dosage forms, often manufactured in the shape of a compressed single layered tablet, comprising a cellulose ether are known to the pharmaceutical drug dispensing art. For example, dosage forms comprising the cellulose ether hydroxypropylmethylcellulose are disclosed in U.S. Pat. Nos. 3,870,790; 4,140,755; 4,167,588; 4,226,849; 4,259,314:, 4,357,469; 4,369,172; 4,389,393 and 4,540,566.

While the dosage forms known to the prior art use the cellulose ether hydroxypropylmethylcellulose for the manufacture of the dosage form, there are major disadvantages associated with the prior art dosage forms. For instance, the mechanical integrity of some prior art dosage forms often is insufficient to provide both a sustained and a controlled release of drug over a prolonged period of time. The prior art dosage forms often exhibit insufficient mechanical integrity, that is, the ability to stay together in a moving fluid environment, such as the gastrointestinal tract, without prematurely breaking-up and prematurely releasing all of its drug. The above-mentioned desirable properties are not apparent in the prior art dosage forms that undergo substantial disintegration in less then eight hours in a fluid environment of use.

Another disadvantage associated with the prior art dosage forms is that the dosage forms frequently exhibit an unwanted, variable and difficult to reproduce release rate pattern. For example prior art dosage forms comprising a small amount of a cellulose ether frequently exhibit this behavior, such as those having less than five weight percent hydroxypropylmethylcellulose having a molecular weight greater than 50,000 and blended with a hydroxypropylmethylcellulose having a molecular weight much less than 50,000 grams per mole. The presence of the high molecular weight polymer in the dosage form masks the release characteristics of the low molecular weight polymer in the dosage form resulting in an erratic release rate pattern which is difficult to reproduce from dosage form to dosage form and from batch to batch of dosage forms.

Still other disadvantages associated with the prior art dosage forms are that the dosage form over its shelf-life can exhibit an unpredictable change in its release rate characteristics; the prior art dosage form when tested in an in vitro test that substantially reproduces the in vivo environment of the gastrointestinal tract often release the drug at a great rate of release in vivo rather than in vitro, which difference can be attributed to a premature disintegration of the prior art dosage form; and, the prior art dosage form in a high shear environment releases its drug too quickly, usually in less than six hours and it is therefore not adapted to prolonged release.

Thus, in the light of the above presentation it will be appreciated by those versed in the dispensing art that if a novel dosage form is made available to the medical and pharmaceutical arts for dispensing difficult to deliver drugs free of the tribulation known to the prior art, such a dosage form would have a definite use and would also be a valuable contribution to the dispensing art. It will be further appreciated by those versed in the dispensing art that if a dosage form can be provided that (a) possesses desirable release rate and mechanical properties for dispensing a drug over a prolonged period of time, and which dosage form (b) can be manufactured at an economical cost, such a dosage form would have a positive and a practical value and also represent an advancement in the pharmaceutical arts.

OBJECTS OF THE INVENTION

Accordingly, it is an immediate object of this invention to provide a novel dosage form for the controlled delivery of a beneficial drug to a biological environment of use, and which dosage form represents an improvement and an advancement in the delivery arts.

Another object of the invention is to provide both a novel and a useful dosage form that overcomes the difficulties associated with the prior art.

Another object of the invention is to provide a dosage form comprising a first lamina and a second lamina comprising a cellulose ether composition with at least one of the laminae comprising a beneficial drug.

Another object of this invention is to provide a dosage form that is useful for delivering a beneficial drug formulation that is difficult to deliver and now can be delivered by the dosage form of this invention at a meaningful therapeutic rate over a prolonged period of time.

Another object of the present invention is to provide a dosage form comprising a beneficial drug that can be from insoluble to very soluble in an aqueous fluid, and which drug can be delivered by the dosage form at an in vitro rate of release that is parallel by the in vivo rate of release.

Another object of this invention is to provide a dosage form that can administer to a warm-blooded host a complete pharmaceutical regimen comprising very soluble or poorly soluble drugs, at a controlled and continuous rate for a particular time period, the use of which requires intervention only for initiation and possible termination of the regimen.

Another object of the present invention is to provide a dosage form for delivering a drug in the gastrointestinal tract that substantially avoids a premature break-up and undergoes a change in its integrity at a rate corresponding to the rate of release of drug over a prolonged period of time at least eight hours.

Other objects, features, aspects and advantages of the invention will be more apparent to those versed in the dispensing art from the following detailed specification taken in conjunction with the drawing figures and the accompanying claims.

BRIEF DESCRIPTION OF THE DRAWINGS

In the drawings, which are not drawn to scale but are set forth to illustrate various embodiments of the invention, the drawing figures are as follow.

In the drawings and in the specification like parts in related figures are identified by like numbers. The terms appearing earlier in the specification and in the drawings, as well as embodiments thereof, are further described elsewhere in this specification.

DETAILED DESCRIPTION OF THE DRAWINGS

Figure 1:
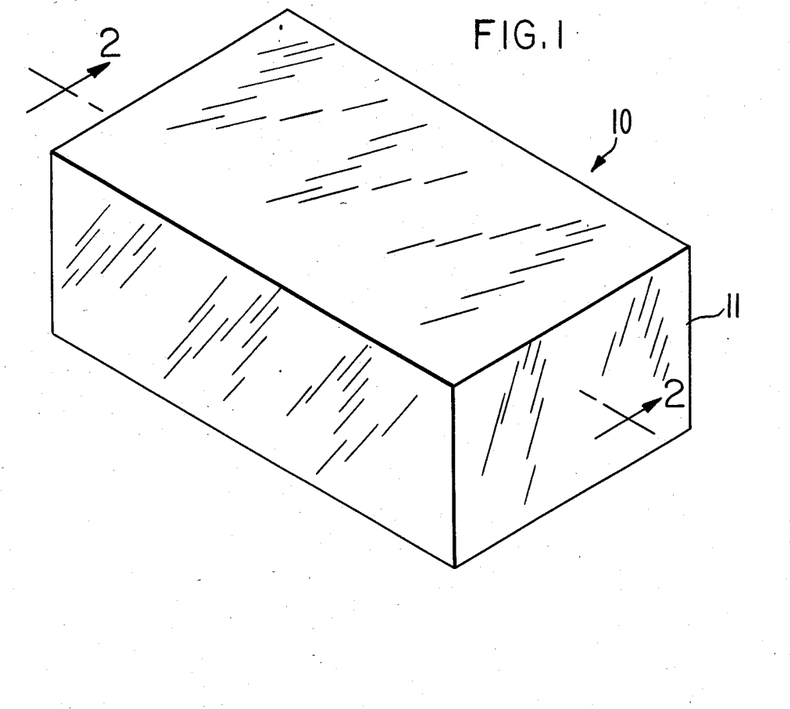
FIG. 1 is a side, elevated view of a dosage form provided by this invention, designed and shaped for orally administering a beneficial drug to the gastrointestinal tract of a recipient.
Figure 2:
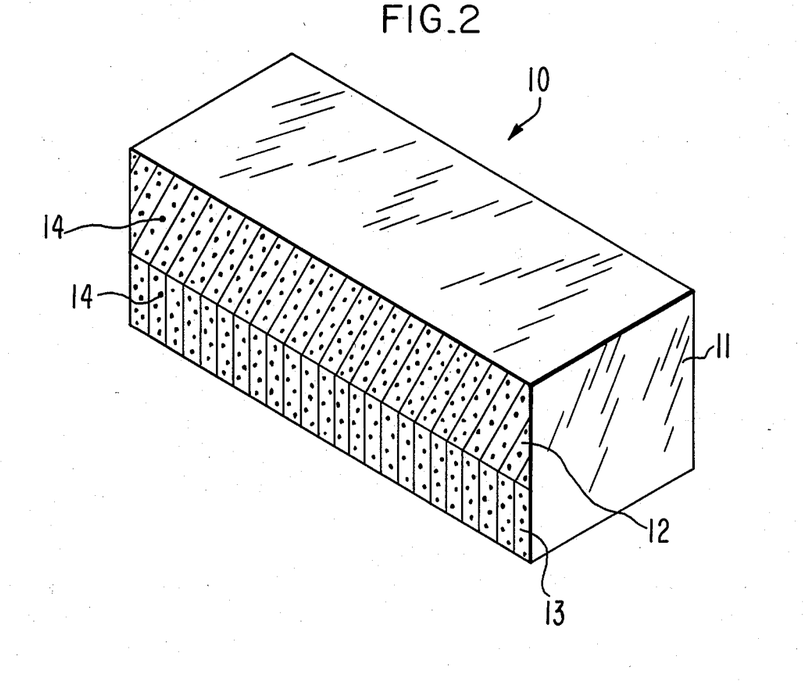
FIG. 2 is an opened view of the dosage form of FIG. 1 through 2—2 of the dosage form for illustrating the internal structure of the dosage form; and, FIGS. 3, 4, 5 and 6 depict release patterns over time for dosage forms provided by this invention.

Turning now to the drawing figures in detail, which drawing figures are an example of the dosage forms provided by the invention, and which example is not to be construed as limiting, one example of this dosage form is illustrated in FIG. 1 and in FIG. 2 and designated by the numeral 10. In FIG. 1, dosage form 10 comprises body 11. Dosage form 10 can be manufactured into various sizes and shapes adapted for oral admittance into the gastrointestinal tract of a warm-blooded animal. For example, dosage form 10 can be of any convenient geometric shape, such as ellipsoid, bean-shaped, circular-shaped, rectangular-shaped, caplet-shaped; and the like.

In FIG. 2, dosage form 10 is seen in opened section through 2—2 of FIG. 1. In FIG. 2 dosage form 10 comprises body 11, which body 11 comprises a first lamina 12 and a second lamina 13. First lamina 12 and second lamina 13 are laminated together and they function in concert as a single dosage form 10. Dosage form 10 comprises at least one beneficial drug 14 present in at least one of first lamina 12, or present in second lamina 13 or, optionally, present in both first lamina 12 and second lamina 13. Dosage form 10 comprising lamina 12 and lamina 13 comprises a non-toxic cellulose ether composition and, optionally, other pharmaceutically acceptable laminae forming ingredients.

Dosage form 10 comprises from about 30 weight percent to 90 weight percent (wt %) of a cellulose ether composition based on the total weight of the dosage form. In a presently preferred embodiment the cellulose ether composition of dosage form 10 comprises at least one hydroxypropylmethylcellulose and at least one hydroxypropylcellulose. The hydroxypropylcellulose operable for the purpose of this invention comprises a hydroxypropoxyl content of 4% to 12% and a methyloxy content 19% to 24%, and the hydroxypropylcellulose comprises a hydropropxyl content of from 7% to 16%. Exemplary hydroxypropylmethylcellulose that can be used for forming dosage form 10 comprises at least one of a member selected from the group consisting of (a) a hydroxypropylmethylcellulose having a degree of polymerization (DP) of about 50, a viscosity of about 3 centipoises of a 2% solution in water, a number average molecular weight of about 9,200; (b) a hydroxypropylmethylcellulose having a DP of 100, a viscosity of 35 centipoises (cps), a number average molecular weight ($MW_n$) of 19,600; (c) a hydroxypropylmethylcellulose comprising a DP of 145, a viscosity of 100 cps, a $MW_n$ of 27,800; (d) a hydroxypropylmethylcellulose comprising a DP of 460, a viscosity of 4,000 cps, a $MW_n$ of 88,300; (e) a hydroxypropylmethylcellulose comprising a DP of 690, a viscosity of 15,000 cps, a $MW_n$ of 132,500; and (f) a hydroxypropylmethylcellulose having a DP of 1260, a viscosity of 100,000 cps, a $MW_n$ of 242,000.

The hydroxypropylcellulose used for the purpose of this invention is a nonionic ether with neutral pH range and a hydroxypropyl content of 7% to 16%, with more specific hydroxypropylcelluloses comprising a hydroxypropyl content of 7% to 10%; a hydroxypropyl content 10% to 13%, and a hydroxypropyl content 13% to 16%. In the above specification DP is the degree of polymerization indicating the number of monomers polymerized in the final polymer and $MW_n$ is the number average molecular weight of the polymer.

Other hydroxypropylmethylcellulose ethers that can be for the purpose of providing dosage form 10 are (g) a hydroxypropylmethylcellulose comprising a DP of 59, a viscosity of 6 and a $MW_n$ of 11,900; and (h) a hydroxypropylmethylcellulose possessing a DP of 860, a viscosity of 30,000 and a $MW_n$ of 165,000. The examples as set forth above generally comprise a hydroxypropylmethylcellulose comprising a DP of 40 to 1600, a viscosity of 2 to 225,000 and a $MW_n$ of from 9,000 to 307,200, and mixtures thereof.

Lamina 12 of dosage form 10 comprises at least one hydroxypropylmethylcellulose in an amount of at least 30 wt % to 80 wt % based on the total weight of dosage form 10, or at least 40 wt % to 80 wt % based on the total weight of lamina 12. Lamina 13 of dosage form 10 comprises at least one hydroxypropylcellulose in an amount of at least 2 wt % to 20 wt % based on the total weight of dosage form 10, or about 10 wt % to 50 wt % based on the total weight of lamina 13. Lamina 12 and lamina 13 can comprise each a single cellulose ether, a blend of two cellulose ethers, a tertiary blend comprising three cellulose ethers, and the like.

Representative of cellulose ether compositions comprising lamina 12 are (a) a composition comprising a hydroxypropylmethylcellulose having a $MW_n$ of about 242,000; (b) a hydroxypropylmethylcellulose having a $MW_n$ of about 132,500; (c) a composition comprising both a hydroxypropylmethylcellulose having a $MW_n$ of 9,200 and a hydroxypropylmethylcellulose having a $MW_n$ of 242,000; (d) a composition comprising a hydroxypropylmethylcellulose having a $MW_n$ of 19,600 and a hydroxypropylmethylcellulose having a $MW_n$ of about 242,000; (e) a composition comprising a hydroxypropylmethylcellulose having a $MW_n$ of about 27,800 and a hydroxypropylmethylcellulose having a $MW_n$ of about 242,000; (f) a composition comprising a hydroxypropylmethylcellulose having a $MW_n$ of 88,300 and a hydroxypropylmethylcellulose having a $MW_n$ of about 242,000; (g) a composition comprising a hydroxypropylmethylcellulose having a $MW_n$ of 132,500 and a hydroxypropylmethylcellulose having a $MW_n$ of about 242,000; (h) a composition comprising a hydroxypropylmethylcellulose having a $MW_n$ of 9,200, a hydroxypropylmethylcellulose having $MW_n$ of 19,600 and a hydroxypropylmethylcellulose having a $MW_n$ of about 242,000; (i) a composition comprising a hydroxypropylmethylcellulose having a $MW_n$ of 9,200, a hydroxypropylmethylcellulose comprising $MW_n$ of 88,300 and a hydroxypropylmethylcellulose having a $MW_n$ of about 242,00; (j) a composition comprising a hydroxypropylmethylcellulose cellulose having a $MW_n$ of 19,600, hydroxypropylmethylcellulose having a $MW_n$ of about 27,800 and a hydroxypropylmethylcellulose having a $MW_n$ of about 242,000; and the like. A binary composition comprising two cellulose ethers in a presently preferred embodiment comprises from 1 wt % to 99 wt % of one cellulose ether and from 99 wt % to 1 wt % of the other cellulose ether. A tertiary composition comprises from 1 wt % to 99 wt % of each cellulose ether with a total cellulose ether content of up to 80 wt % based on the total weigh of lamina 12.

Lamina 13, in one presently preferred embodiment, comprises from 2 wt % to 30 wt % of a single low substituted hydroxypropylcellulose ether having a hydroxypropyl content of 7% to 16%. Lamina 13 in other preferred embodiments comprises (a) a binary blend of a hydroxypropylcellulose having a hydroxypropyl content of 7 to 10 wt % blended with a hydroxypropylcellulose having a hydroxypropyl content of 13 to 16 wt %; (b) a composition comprising a hydroxypropylcellulose having a hydroxypropyl content of 7 to 10 wt % blended with a hydroxypropylcellulose having a hydroxypropyl content of about 10 to 13 wt %; (c) a composition comprising a hydroxypropylcellulose and a hydroxypropylmethylcellulose having a $MW_n$ of 9,200; (d) a composition comprising a hydroxypropylcellulose and a hydroxypropylmethylcellulose having a $MW_n$ of about 19,600; (e) a hydroxypropylcellulose and a hydroxypropylmethylcellulose having a $MW_n$ of 27,800 ; (f) a composition comprising a hydroxypropylcellulose and a hydroxypropylmethylcellulose having a $MW_n$ of about 88,300; (g) a composition comprising a hydroxypropylcellulose and a hydroxypropylmethylcellulose having a $MW_n$ of about 132,500; (h) a composition comprising a hydroxypropylcellulose and a hydroxypropylmethylcellulose having a $MW_n$ of about 242,000; and the like.

Dosage form 10 comprises a beneficial drug 14. Drug 14 can be presented in lamina 12; drug 14 can be presented in lamina 13, and drug 14 can be presented in both lamina 12 and lamina 13. In this specification the term "drug" includes any physiologically or pharmacologically active substance that produces a local or systemic effect in animals, including warm-blooded mammals, humans and primates; avians; household, sport and farm animals; laboratory animals; fishes, reptiles and zoo animals. The term "physiologically", as used herein, denotes the administration of a drug to produce generally normal levels and functions in a warm-blooded animal. The term "pharmacologically" generally denotes variations in response to the amount of drug administered to the host. See *Stedman's Medical Dictionary*, 1966, published by Williams and Wilkins, Baltimore, Md.

The active drug that can be delivered includes inorganic and organic compounds without limitation, including drugs that act on the peripheral nerve, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, organ systems, reproductive system, skeletal system, autocoid systems, alimentary and excretory systems, inhibitors of autocoids and histamine systems. The active drug that can be delivered for acting on these recipients include anticonvulsants, analgesics, anti-parkinsons, anti-inflammatories, anesthetics, antimicrobials, antimalarials, antiparasitic, antihypertensives, angiotensin converting enzyme inhibitor, antihistamines, antipyretics, alpha-adrenergic agnoist, alpha-blockers, biocides, bactericides, bronchial dilators, beta-adrenergic stimulators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, and the like.

Exemplary drugs that are very soluble in water can be delivered by dosage form 10 of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodine, tridihexethyl chloride, phenformin hydrochloride, methylphenidate hydrochloride, cimetidine hydrochloride, theophylline cholinate, cephalexin hydrochloride, and the like.

Exemplary drugs that are poorly soluble in water and that can be delivered by dosage form 10 of this invention include diphenidol, meclizine hydrochloride, prochlorperazine maleate, phenoxybenzamine, thiethylperazine maleate, anisindone, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate acetyl sulfisoxazole, erythromycin, progestins, esterogenic, progestational, corticosteroids, hydrocortisone, hydrocorticosterone acetate, cortisone acetate, triamcinolone, methyltesterone, 17-beta-estradiol, ethinyl estradiol, prazosin hydrochloride, ethinyl estradiol 3-methyl ether, pednisolohe, 17alpha-hydrocyprogesterone acetate, 19-nor-progesterone, norgestrel, norethindrone, progesterone, norgesterone, norethynodrel, and the like.

Examples of other drugs that can be delivered by dosage form 10 include aspirin, indomethacin, naproxen, fenoprofen, sulindac, indoprofen, nitroglycerin, propranolol, timolol, atenolol, alprenolol, cimetidine, clonidine, imipramine, levodopa, chloropromazine, methyldopa, dihydroxyphenylalnine, pivaloyloxyethyl ester of alpha-methyldopa, theophylline, calcium gluconate, ketoprofen, ibuprofen, cephalexin, erythromycin, haloperidol, zomepirac, ferrous lactate, vincamine, diazepam, captopril, phenoxybenzamine, nifedipine, diltiazem, verapamil, milrinone, madol, quanbenz, hydrochlorothiazide, and the like. The beneficial drugs are known to the art in *Pharmaceutical Sciences*, 14th Ed., edited by Remington, (1979) published by Mack Publishing Co., Easton, Pa.; *The Drug, The Nurse, The Patient, Including Current Drug Handbook*, by Falconer et al., (1974–1976) published by Sunder Co., Philadelphia, Pa.; *Medicinal Chemistry*, 3rd Ed., Vol. 1 and 2, by Burger, published by Wiley-Interscience, New York and in *Physicians' Desk Reference*, 38 Ed., (1984) published by Medical Economics Co., Oradell, NJ.

The drug in dosage form 10 can be in various forms, such as uncharged molecules, molecular complexes, pharmacologically acceptable salts such as hydrochloride, hydrobromide sulfate, laurate, palmitate, phosphate, nitrite, borate, acetate, maleate, tartrate, oleate and salicylate. For acidic drugs, salts of metals, amines or organic cations; for example, quaternary ammonium can be used. Derivatives of drugs such as ester, ethers and amides can be used. Also, a drug that is water insoluble can be used in a form that is a water soluble derivative thereof to serve as a solute, and on its release from the device is converted by enzymes, hydrolyzed by body pH or other metabolic processes to the original biologically active form.

Drug 14 can be present in dosage form 10 neat or, as in a presently preferred optional embodiment, with a binder, dispersant, wetting agent, lubricant or dye. Representative of these include acacia, agar, calcium carrageenan, alginic acid, algin, agarose powder, collagen, colloidal magnesium silicate, pectin, gelatin, and the like; binders like polyvinyl pyrrolidone; lubricants such as magnesium stearate; wetting agent such as fatty amines, fatty quaternary ammonium salts, ester of sorbitol, and the like. The phrase drug formulation indicates the drug is present in dosage form 10 neat or accompanied by a binder, and the like. The amount of beneficial drug in dosage form 10 generally is from about 0.05 ng to 5 g or more, with individual dosage form 10 comprising for example, 25 ng, 1 mg, 5 mg, 10 mg, 25 mg, 250 mg, 750 mg, 1.0 g, 1.2 g, 1.5 g, and the like. In a presently preferred embodiment lamina 12 comprises more drug 14 than does lamina 13; however, the amount of drug 14 can be the same. Generally, the amount of drug will be in a ratio in lamina 12 to lamina 13 in a ratio of 1:1 to 15:1. The dosage form can be administered once, twice or three times daily.

Dosage form 10 is manufactured by first making independently lamina 12, or lamina 13, which laminae are made from a well-mixed composition of laminae forming members. For example, a particular lamina is made as follows: first, each of the ingredients comprising a lamina are independently screened and then blended together, except for the lubricant. Then the homogeneous blend is wet granulated by adding a solvent such a anhydrous ethanol, and the wet ingredients mixed until a uniform blend is obtained by said process. Next, the wet blend is passed through a screen and dried to evaporate the solvent. The resulting granules are passed again through a sieve. Next, a small amount of a finely divided lubricant is added to the dry granules and the lubricant and granules blended to provide a uniform blend. Next, the above described procedure is repeated for the other lamina.

Next, the two lamina forming compositions are fed independently into separate hoppers of a compression machine. The machine lightly compresses one lamina and then adds the second lamina forming granulation in laminating arrangement to the first lamina and then compresses the two laminae together. Typically, about two tons of pressure are applied to laminate the laminae and yield the final dosage form.

The dosage form can be made also by a dry granulation process of manufacture. The dry process comprises first mixing, for a particular lamina, all the lamina forming ingredients, except for the lubricant, passing the mixed ingredients through a grinding mill to a small mesh size, and then transferring the sized powder to a dry compactor. The compactor densifies the powder, which dense powder is then passed through a sizing mill to regrind the composition. The composition is ground to a small size, typically 20 mesh or smaller. Finally, a dry lubricant is added and the ingredients blended to produce the final lamina forming composition. The second lamina is made in a similar manner. Then, each composition is fed independently to the compaction press and compressed into the dosage form comprising parallel laminae.

Other standard manufacturing procedures can be used to form the laminae and the laminated dosage form. For example, the various ingredients can be mixed with a solvent by ballmilling, calendering, stirring or rollmilling, and then pressed into a preselected sized and shaped lamina. A second lamina made in a like process comprising a shape and size corresponding to the first lamina is then laminated with pressure to the first lamina to yield the dosage form.

Exemplary solvents suitable for manufacturing the lamina include inorganic and organic solvents that do not adversely harm the lamina, the lamina formin ingredients and the final dosage form. The solvents broadly include a member selected from the group consisting of alcohols, ketones, esters, ethers, aliphatic hydrocarbons, halogenated solvents, cycloaliphatic solvents, aromatic, heterocyclic solvents, and mixtures thereof. Typical solvents include acetone, diacetone, methanol, ethanol, isopropyl alcohol, butyl alcohol, methyl acetate, ethyl acetate, isopropyl acetate, n-butylacetate, methyl isobutyl ketone, methyl propyl ketone, n-hexane, h-heptane, methylene dichloride, ethylene dichloride, propylene dichloride, ethyl ether, mixtures such as acetone and ethanol, acetone and methanol, methylene dichloride and methanol, ethylene dichloride and methanol, and the like.

The following examples illustrate means and methods for carrying out the present invention. The examples are merely illustrative and they should not be considered as limiting the scope of the invention, as these examples and other equivalents thereof will become more apparent to those versed in the pharmaceutical dispensing art in the light of the present disclosure, the drawing and the accompanying claims.

EXAMPLE 1

A lamina forming composition comprising 29.5 wt % isosorbide dinitrate, 29.5 wt % lactose, 40.0 wt % hydroxypropylmethylcellulose, having an average molecular weight of 27,800 and 1.0 wt % magnesium stearate is compressed into a first lamina. Next, a second lamina forming composition comprising 97.0 wt % hydroxypropylmethylcellulose having a molecular weight of 242,000, 1.0 wt % ferric oxide and 2.0 wt % magnesium stearate is deposited over the first lamina and the second lamina laminated to the first lamina with a compression of 2 tons. The first lamina weighed 271 mg and the second lamina weighed 100 mg. The laminae are compressed in a 13/32 inch round dye. The dosage form released pattern measured in a shaking flask containing water and a few marbles for producing mechanical abuse, exhibited a cumulative release of 98% over a 24 hour period of time. Lamina 1 comprising the lower molecular weight cellulose either erodes in the aqueous environment and administers the drug over time. Lamina 2 comprising the higher molecular weight ether maintains its mechanical integrity longer because of its composition. Lamina 2 serves as a support member for lamina 1.

EXAMPLE 2

Figure 3:
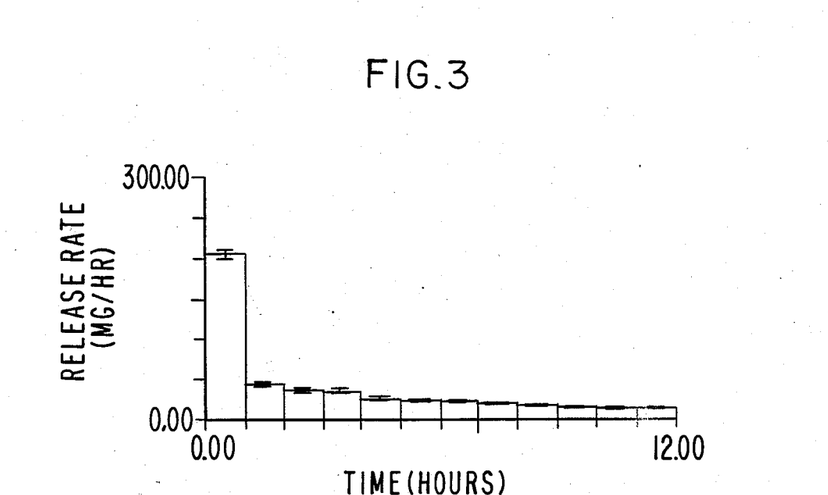
Figure 4:
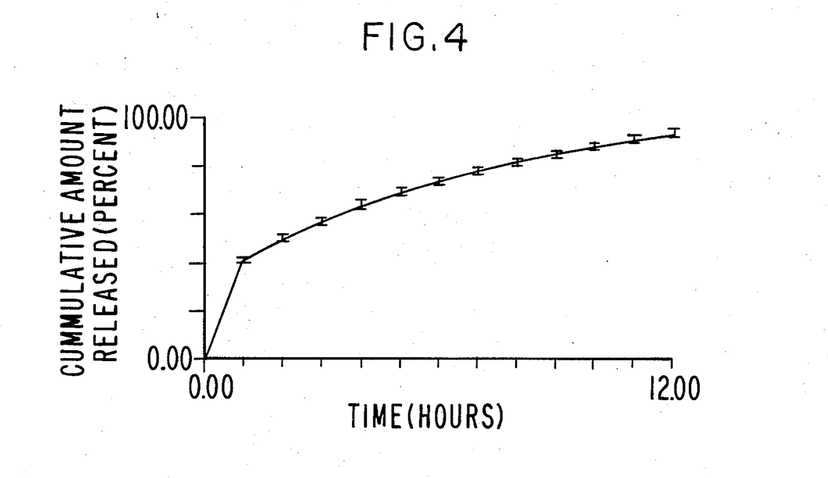

The procedures described above are followed in this example. First a lamina forming composition comprising 58.0 wt % acetaminophen, 25.0 wt % hydroxypropylmethylcellulose having a number average molecular weight of 242,000, a number average degree of polymerization of about 1260 and a viscosity of 100,000 centipoises, 15.0 wt % hydroxypropylmethylcellulose having a number average molecular weight of 9,200 a number average degree of polymerization of 50 and a viscosity of 3 centipoises, and 2.0 wt % magnesium stearate is compressed into a first lamina. The lamina weighed 604 mg. Then, a second lamina forming composition weighing 170.5 mg and comprising 88.0 wt % acetaminophen, 10.0 wt % hydroxypropylcellulose with 10–13 wt % hydroxypropxy content, and 2.0 wt % magnesium stearate is laminated to the first lamina to yield the dosage form. The release rate measured in mg/hr for this bilaminated dosage form is depicted in FIG. 3. The cumulative amount of acetaminophen released over a percent basis over a a 12 hour period of time is depicted in FIG. 4. The dosage form exhibited in initial release of 200 mg drug within the first hour, followed by a mean release rate of 24 mg per hour for the next eleven hours.

EXAMPLE 3

Figure 5:
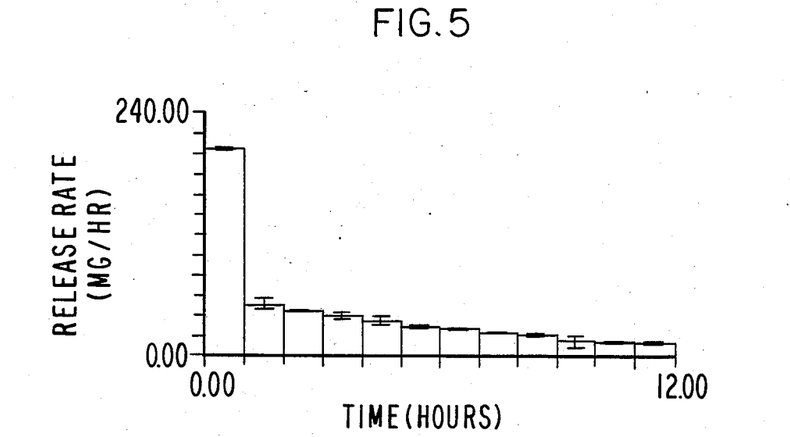
Figure 6:
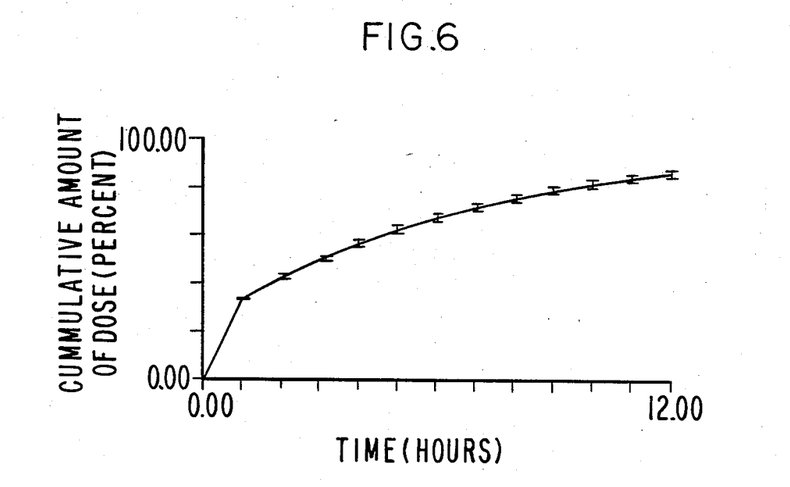

The procedure described above is followed in this example. A first lamina forming composition weighing 690 mg and comprising 58.0 wt % ibuprofen, 25.0 wt % hydroxypropylcellulose having a number average molecular weight of 242,000, 15.0 wt % hydroxypropylmethylcellulose having a number average molecular weight of 9,200, and 2.0 wt % stearic acid is compressed into a first lamina. Then a second lamina weighing 230 mg comprising 87.0 wt % ibuprofen, 10.0 wt % hydroxypropylcellulose with 10–13 wt % hydroxypropxy content, 2.0 wt % hydroxypropylmethylcellulose having an average number molecular weight of 9,200, and 2.0 wt % stearic acid is deposited over a surface of the first lamina and the second lamina compressed thereto. The dosage form exhibited an initial burst of 200 mg drug within the first hour followed by a mean release rate of 28 mg/hr for the following eleven hours. The release rate in mg/hr is illustrated in FIG. 5. The cumulative amount of ibuprofen released over time is illustrated in FIG. 6.

EXAMPLES 4 TO 21

The procedures described above are followed for manufacturing dosage forms comprising the following drugs: (a) 150 mg of ibuprofen in the first lamina and 50 mg of ibuprofen in the second lamina; (b) 400 mg of ibuprofen in the first lamina and 200 mg of ibuprofen in the second lamina; (c) 300 mg of aspirin in the first lamina and 200 mg of aspirin in the second lamina; (d) 400 mg of cimetidine in the first lamina and 200 mg of cimetidine in the second lamina; (e) 200 mg of umetidine in the first lamina and 100 mg of umetidine in the second lamina; (f) 100 mg of ranitidine in the first lamina and 50 mg of ranitidine in the second lamina; (g) 250 mg of acetaminophen in the first lamina and 250 mg of acetaminophen in the second lamina; (h) 250 mg of aspirin in the first lamina and 20 mg of caffeine in the second lamina; (i) 150 mg of aspirin in the first lamina and 12 mg of caffeine in the second lamina; (j) 350 mg of naproxen in the first lamina and 175 mg of naproxen in the second lamina; (k) 50 mg of phenylpropanolamine in the first lamina and 25 mg phenylpropanolamine in the second lamina; (l) 80 mg of pseudoephedrine in the first lamina and 40 mg of pseudoephedrine in the second lamina; (m) 40 mg of pseudoephedrine hydrochloride in the first lamina and 20 mg of pseudoephedrine hydrochloride in the second lamina; (n) 20 mg of pseudoephedrine in the first lamina and 1 mg of chlorpheniramine maleate in the second lamina; (o) 40 mg of pseudoephedrine in the first lamina and 3 mg of chlorpheniramine maleate in the second lamina; (p) acetaminophen in the first lamina and codeine in the second lamina; and (q) ibuprofen in the first lamina and codeine in the second lamina.

EXAMPLE 22

A dosage form for the controlled and the continuous administration of the drug 6-methoxy-alpha-methyl-2-naphthaleneacetic acid is prepared by following the above described process of manufacture. The dosage form is manufactured by making a first lamina comprising 59 wt % of the drug, with 39 wt % low molecular weight hydroxypropylmethylcellulose having an average number molecular weight of 19,600; a number average degree of polymerization of 100; and a viscosity of 35 centipoises; a second lamina comprising 1 wt % hydroxypropylcellulose with a 10–13 wt % hydroxypropxy content and 1 wt % magnesium stearate and a different hydroxypropylmethylcellulose having an average number molecular weight of 242,000; a number average degree of polymerization of 1260 and a viscosity of 100,000 centipoises measured as a 2% aqueous solution at 20° C., was laminated to the first lamina. The two lamina operated as a unit dosage form for the release of the drug at a controlled rate over time.

EXAMPLE 23

A dosage form for the controlled and the continuous administration of isosorbide dinitrate is prepared by following the above described process of manufacture. The dosage form is manufactured by making a first lamina comprising 59 wt % isosorbide/lactose, 50/50, with 39 wt % low molecular weight hydroxypropylmethylcellulose having an average number molecular weight of 27,000; a number average degree of polymerization of 145 and a viscosity of 100 centipoises; and a second lamina comprising 1 wt % hydroxypropylcellulose having a 10–13 wt % hydroxypropxy content; 97 wt % of a different hydroxypropylmethylcellulose having an average number molecular weight of about 242,000; a number average degree of polymerization of 1260; a viscosity of 100,000 centipoises measured as a 2% aqueous solution as 20% C; 1% ferric oxide and 1 wt % magnesium stearate.

EXAMPLE 24

Dosage form 10 of this invention provides many advantages to the dispensing art. For example, the bilaminated structure of dosage for 10 comprises a fast drug releasing lamina 12 and a slower drug releasing lamina 13. The fast drug releasing lamina 12 begins to dispense drug 14 immediately for producing an initial plasma concentration of drug 14 in a warm-blooded animal, which expression includes humans. The slower drug releasing lamina 13 releases drug 14 continuously and over time for producing a steady-state drug 14 concentration. The expression "fast drug 14 releasing lamina 12 and slower drug 14 releasing lamina 13" as used for the purpose of this invention, denotes that lamina 12 releases drug 14 at a faster rate per unit time than does lamina 13. Also, lamina 13 because of its physical properties provides mechanical support for lamina 12 thereby extending its drug releasing period over time. Another advantage provided by dosage form 10 is that it exhibits stomach retention during part of its drug releasing life. This stomach retention provides release of drug 14 in the stomach for drug absorption in the upper gastrointestinal tract. This retention in the upper gastrointestinal tract and delivery of drug from the stomach allows the drug to be absorbed throughout the gastrointestinal tract. This delivery system is particularly useful for drugs with known absorption windows in the upper tract.

Additional advantages of dosage form 10 are its release of drug 14 at a rate independent of the pH of the environment of use, dosage form 10 releases drug 14 at about the same rate per unit time in artificial stomach fluid and in artificial intestinal fluid, dosage form 10 releases drug 14 substantially free of irritating laboratory mucosal tissue, and eventually dosage form 10 fully erodes and dissolves in the gastrointestinal tract substantially free of residual particles.

The novel dosage form of this invention comprises means for the obtainment of precise release rate in the environment of use while simultaneously providing beneficial therapy to a recipient. While there has been described and pointed out features of the invention as applied to presently preferred embodiments, those skilled in the dispensing art will appreciate that various modification, changes, additions and omissions in the dosage form illustrated and described can be made without departing from the spirit of this invention.

We claim:

1. A bilaminated system for delivering a beneficial drug to an environment of use, the bilaminated system comprising: 30 weight percent to 90 weight percent of a cellulose ether composition: said composition comprising a first lamina comprising up to 80 weight percent of a cellulose ether selected from the group of hydroxypropylmethylcellulose ethers comprising a degree of polymerization of about 50 to 1260, a viscosity of about 3 to 100,000 centipoises, and a number average molecular weight of 9,000 to 250,000, and a dosage amount of from 0.05 ng to 5 g of a beneficial drug; and, a second lamina in contacting arrangement with the first lamina, the second lamina comprising up to 50 weight percent of a different cellulose ether composition comprising a hydroxypropylcellulose comprising a hydroxypropxyl content of 7% to 16%.

2. The bilaminated system for delivering a beneficial drug to an environment of use according to claim 1, wherein the second lamina comprises up to 80 weight percent of a hydroxypropylmethylcellulose ether comprising a degree of polymerization of about 50 to 1260, a viscosity of about 3 to 100,000 centipoises, and a number average molecular weight of from about 9,000 to 250,000.

3. The bilaminated system for delivering a beneficial drug to an environment of use according to claim 1, wherein the second lamina comprises a dosage amount of from 0.05 ng to 5 g of a beneficial drug.

4. The bilaminated system for delivering a beneficial drug to an environment of use according to claim 1, wherein the second lamina comprises a hydroxypropylmethylcellulose ether having a number average molecular weight of from about 9,000 to 250,000 and a dosage amount of from 0.05 ng to 5 g of a beneficial drug.

5. The bilaminated system for delivering the beneficial drug to the environment of use according to claim 1, wherein the second lamina comprises a hydroxypropylmethylcellulose ether having a number average molecular weight of from about 9,000 to 250,000, a dosage amount of from 0.05 ng to 5 g of a beneficial drug, and wherein the second lamina releases more drug per unit time than the first lamina releases drug per unit time and erodes at a faster rate of erosion than the first lamina when the bilaminated system is in an environment of use comprising an aqueous fluid.

6. The bilaminated system for delivering the drug to an environment of use according to claim 1, wherein the drug in the first lamina is a member selected from the group consisting of ibuprofen, acetaminophen and codeine; and wherein the second lamina comprises a dosage amount of a drug selected from the group consisting of ibuprofen, acetaminophen and codeine.

7. The bilaminated system for delivering the beneficial drug to an environment of use according to claim 1, wherein the first lamina comprises more than one different hydropropylmethylcellulose ether.

8. A bilaminated system for delivering a beneficial drug to an environment of use, the bilaminated system comprising: (a) a cellulose ether composition comprising: (b) a first lamina comprising up to 80 weight percent of a cellulose ether selected from the group consisting of hydroxypropylmethylcellulose ethers comprising a degree of polymerization of 40 to 1600, a viscosity of 2 to 225,000 and a number average molecular weight of 9,000 to 307,200; and (c) a second lamina in parallel mated relation with the first lamina, the second lamina comprising up to 50 weight percent of a cellulose ether composition comprising a hydroxypropylcellulose comprising a hydroxypropoxyl content of 7 percent to 16 percent, and a dosage unit amount of 25 ng to 1.5 g of a beneficial drug.

9. The bilaminated system for delivering a beneficial drug to an environment of use according to claim 8, wherein the second lamina comprises a hydroxypropylmethylcellulose ether comprising a degree of polymerization of 40 to 1600, a viscosity of 2 to 225,000, and a number average molecular weight of from 9,000 to 307,200.

10. The bilaminated system for delivering a beneficial drug to an environment of use according to claim 8, wherein the first lamina comprise more than one hydroxypropylmethylcellulose ether.

11. A bilaminated system for delivering a beneficial drug to an environment of use, wherein the bilaminated system comprises: (a) at least 30 weight percent of a cellulose ether composition present in a first lamina and a second lamina; wherein the first lamina comprises up to 85 weight percent of at least one hydropropylmethylcellulose comprising a number average molecular weight of from 9,000 to 250,000; and wherein the second lamina comprises up to 85 weight percent of hydroxypropylmethylcellulose comprising a different number average molecular weight of from 9,000 to 250,000 and a dosage amount of from 25 ng to 1.5 g of a beneficial drug.

12. The bilaminated system for delivering the beneficial drug to the environment of use according to claim 10, wherein the first lamina comprises more than one hydroxypropylmethylcellulose.

13. The bilaminated system for delivering the beneficial drug to the environment of use according to claim 10, wherein the second lamina comprises more than one hydroxypropylmethylcellulose ether.

14. A bilaminated system for delivering a beneficial drug to an environment of use, wherein the bilaminated system comprises: (a) 30 weight percent to 90 weight percent of a cellulose ether composition comprising a first lamina and a second lamina; said first lamina comprising a cellulose ether selected from a hydropropylmethylcellulose ether comprising a number average molecular weight of from 9,000 to 250,000 and a dosage unit amount of 25 ng to 1.5 g of a beneficial drug; and wherein the second lamina comprises a cellulose ether selected from a hydroxypropylmethylcellulose ether comprising a different number average molecular weight of from 9,000 to 250,000.

15. The bilaminated system for delivering the beneficial drug to the environment of use according to claim 14, wherein the first lamina comprises more than one cellulose ether and the second lamina comprises more than one cellulose ether.

16. A bilaminated system for delivering the beneficial drug ibuprofen to an environment of use, wherein the bilaminated system comprises: a first lamina comprising up to 80 weight percent of a hydroxypropylmethylcellulose comprising a degree of polymerization of about 50 to 1260, a viscosity of about 3 to 100,000 centipoises and a number average molecular weight of 9,000 to 250,000, and a dosage amount of from 25 ng to 1.5 g of ibuprofen; and a second lamina comprising up to 50 weight percent of a hydroxypropylcellulose comprising from 7 percent to 16 percent hydroxypropoxyl, and a dosage amount of from 25 ng to 1.5 g of ibuprofen.

17. The bilaminated system for delivering the bewneficial drug ibuprofen to an environment of use according to claim 16, wherein the first lamina comprises up to 80 weight percent of a different hydropyleme-thylcelluose comprising a degree of polymerization of about 50 to 1260, a viscosity of about 3 to 100,000 centipoises, and a number average molecular weight of from 9,000 to 250,000.

18. The bilaminated system for delivering the beneficial drug ibuprofen to an environment of use according to claim 16, wherein the second lamina comprises up to weight percent of a different hydropropylmethylcelluose comprising a degree of polymerization of about 50 to 1260, a viscosity of about 3 to 100,000 centipoises and a number average molecular weight of from 9,000 to 250,000.

19. The bilaminated system for delivering the beneficial drug ibuprofen to an environment of use according to claim 16, wherein the first lamina comprises 58 weight percent ibuprofen, and the second lamina comprises 87 weight percent ibuprofen.

20. The bilaminated system for delivering the beneficial drug ibuprofen to an environment of use according to claim 16, wherein the bilaminated system comprises 200 mg of ibuprofen.

21. The bilaminated system for delivering the beneficial drug ibuprofen to an environment of use according to claim 16, wherein the bilaminated system comprises 400 mg of ibuprofen.

22. The bilaminated system for delivering the beneficial drug ibuprofen to an environment of use according to claim 16, wherein the bilaminated system compriss 600 mg of ibuprofen.

23. The bilaminated system for delivering the beneficial drug ibuprofen to an environment of use according to claim 16, wherein the first lamina comprises 400 mg of ibuprofen and the second lamina comprises 200 mg of ibuprofen.

24. The bilaminated system for delivering the beneficial drug ibuprofen to an environment of use according to claim 16, wherein the first lamina comprises a hydropropylmethylcellulose comprising a molecular weight about 9,200 and a hydropropylmethylcellulose comprising a molecular weight about 241,900, and the second lamina comprises a hydroxypropylmethylcellulose comprising a molecular weight about 9,200.

25. A bilaminated system for delivering a beneficial drug to an environment of use wherein the bilaminated system comprises: a first lamina comprising up to 80 weight percent of a hydroxypropylmethylcellulose comprising a degree of polymerization of about 50 to 1260, a viscosity of about 3 to 100,000 centipoises and a number average molecular weight of 9,000 to 250,000; a second lamina comprising a hydroxypropylcellulose comprising a hydroxypropoxyl content of 7% to 16%; and wherein the bilaminated system comprises from 25 ng to 1.5 g of a beneficial drug selected from the group consisting of cimentidine, umetidine, ranitidine, naproxen, estrogenic, progestiational, captopril, diltiazom, and isosorbide dinitrate.

26. The bilaminated system for delivering a beneficial drug to an environment of use according to claim 8, wherein the bilaminated system is sized and shaped for oral administration into the gastrointestinal tract of an animal and thr first lamina comprises more than one hydroxypropylmethylcellulose and a dosage unit amount of a beneficial drug.

* * * * *

UNITED STATES PATENT AND TRADEMARK OFFICE
CERTIFICATE OF CORRECTION

PATENT NO. : 4,786,503
DATED : November 22, 1988
INVENTOR(S) : David E. Edgren, Judy A. Magruder, Gurdish K. Bhatt It is certified that error appears in the above-indentified patent and that said Letters Patent is hereby corrected as shown below:

On the title page, item [54] and in column 1, line 1, in the title "DOSAGE FORM COMPRISING PARALLEL LAMINE" should read --DOSAGE FORM COMPRISING PARALLEL LAMINAE--.

Signed and Sealed this

Third Day of January, 1995

*Attest:*

BRUCE LEHMAN

*Attesting Officer*     *Commissioner of Patents and Trademarks*